(12) United States Patent
Wiggins et al.

(10) Patent No.: US 10,390,758 B2
(45) Date of Patent: Aug. 27, 2019

(54) METHOD AND APPARATUS FOR TRIAGE AND SUBSEQUENT ESCALATION BASED ON BIOSIGNALS OR BIOMETRICS

(71) Applicant: Samsung Electronics Co., Ltd., Suwon-si (KR)

(72) Inventors: Matthew C. Wiggins, San Jose, CA (US); Euan S. Thomson, Los Gatos, CA (US)

(73) Assignee: Samsung Electronics Co., Ltd. (KR)

( * ) Notice: Subject to any disclaimer, the term of this patent is extended or adjusted under 35 U.S.C. 154(b) by 223 days.

(21) Appl. No.: 15/145,356

(22) Filed: May 3, 2016

(65) Prior Publication Data

US 2017/0273620 A1    Sep. 28, 2017

Related U.S. Application Data

(60) Provisional application No. 62/313,053, filed on Mar. 24, 2016.

(51) Int. Cl.
| | |
|---|---|
| *A61B 5/00* | (2006.01) |
| *A61B 5/024* | (2006.01) |
| *A61B 5/0402* | (2006.01) |
| *A61B 5/16* | (2006.01) |
| *A61B 5/01* | (2006.01) |
| *A61B 5/0404* | (2006.01) |
| *A61B 5/053* | (2006.01) |
| *A61B 5/145* | (2006.01) |

(52) U.S. Cl.
CPC ............ *A61B 5/681* (2013.01); *A61B 5/0015* (2013.01); *A61B 5/02416* (2013.01); *A61B 5/02438* (2013.01); *A61B 5/0402* (2013.01); *A61B 5/165* (2013.01); *A61B 5/7203* (2013.01); *A61B 5/742* (2013.01); *A61B 5/746* (2013.01); *A61B 5/7475* (2013.01); *A61B 5/01* (2013.01); *A61B 5/0404* (2013.01); *A61B 5/0533* (2013.01); *A61B 5/14546* (2013.01); *A61B 5/486* (2013.01)

(58) Field of Classification Search
None
See application file for complete search history.

(56) References Cited

U.S. PATENT DOCUMENTS

| | | | |
|---|---|---|---|
| 3,717,857 A | 2/1973 | Evans | |
| 3,731,311 A | 5/1973 | Williams | |
| 3,768,014 A | 10/1973 | Smith et al. | |
| 3,776,228 A | 12/1973 | Semler | |
| 3,779,237 A | 12/1973 | Goeltz et al. | |
| 8,920,332 B2 * | 12/2014 | Hong ................ | A61B 5/02427 600/309 |

(Continued)

FOREIGN PATENT DOCUMENTS

| | | |
|---|---|---|
| CH | 675675 | 10/1990 |
| CN | 1798522 | 7/2006 |
| WO | 2015150199 | 10/2015 |

OTHER PUBLICATIONS

European Search Report for Appln. No. 17154329.1-1657 dated Jul. 10, 2017.

*Primary Examiner* — Brian T Gedeon
(74) *Attorney, Agent, or Firm* — McAndrews, Held & Malloy, Ltd.

(57) ABSTRACT

Provided is an electronic device to monitor a user's biological measurements in two stages, where the first stage determines whether to make measurements and/or appraisals in the second stage.

21 Claims, 5 Drawing Sheets

(56) References Cited

U.S. PATENT DOCUMENTS

| | | | |
|---|---|---|---|
| 8,998,815 B2* | 4/2015 | Venkatraman | A61B 5/721 |
| | | | 600/481 |
| 9,339,202 B2* | 5/2016 | Brockway | A61B 5/0402 |
| 9,560,994 B2* | 2/2017 | McCutcheon | A61B 5/14551 |
| 9,839,363 B2 | 12/2017 | Albert | |
| 2015/0250396 A1 | 9/2015 | Ahmed et al. | |
| 2015/0272510 A1 | 10/2015 | Chin | |
| 2016/0206212 A1* | 7/2016 | Lee | A61B 5/0205 |

* cited by examiner

METHOD AND APPARATUS FOR TRIAGE AND SUBSEQUENT ESCALATION BASED ON BIOSIGNALS OR BIOMETRICS

RELATED APPLICATION(S)

This application claims the benefit of the U.S. Provisional Application 62/313,053, filed on Mar. 24, 2016, the disclosure of which is incorporated herein in its entirety by reference.

BACKGROUND

The present disclosure relates to measuring a user's body signals, and more particularly, to a method and apparatus for using triage and subsequent escalation based on biosignals or biometrics.

Wearable sensor devices that provide biosignals typically have inherent trade-offs. For example, a wearable device that provides more background monitoring typically requires less user involvement. In another example, a wearable device that provides less sensitive signal quality typically has longer battery life. A wearable device that provides less sensitive signal quality may also have better user comfort/acceptance. Typically, longer battery life can be provided for a wearable device by providing less information content. Therefore, a wearable sensor device typically provides background monitoring with maximum user comfort/acceptance, long battery life, and less sensitive sensor signals.

Some wearable sensors can continuously acquire information from a user without the user's participation, thus allowing unobtrusive, near continuous monitoring for abnormal conditions or providing a trend for health, fitness, wellness, and/or disease states. Although such wearable sensors (e.g., a photoplethysmogram (PPG), a galvanic skin response (GSR) sensor, a bioimpedence sensor, a skin temperature sensor, and an oximeter) provide useful information, these sensors are typically sensitive to noise contamination due to motion or variable skin contact. These sensors may also not be as clinically researched/accepted and are therefore less relevant for diagnostic evaluation.

Other sensors and/or diagnostic procedures, though more clinically accepted and relevant, may be less convenient to use for the user. Therefore, data from such sensors are not able to be collected by near continuous monitoring (e.g., electrocardiogram (ECG), impedance cardiograph (ICG), core body temperature, and nystagmus test).

SUMMARY

Provided are method and apparatus for continuous triage and subsequent escalation based on biosignals or biometrics. According to an exemplary embodiment, a method may include acquiring first signals in a first mode from a user via a first sensor of a user-wearable device, and processing the first signals to determine whether to enter a second mode to provide further information to the user. Another exemplary embodiment may include a first sensor of a user-wearable device configured to acquire first signals in a first mode from a user, and a diagnostic processor configured to process the first signals to determine whether to enter a second mode to provide further information to the user. Another exemplary embodiment may include a non-transitory machine-readable medium storing machine executable instructions that when executed causes a computing system to control operations comprising acquiring first signals in a first mode from a user by a first sensor of a user-wearable device, and processing the first signals by a diagnostic processor to determine whether to enter a second mode to provide further information to the user.

Additional aspects will be set forth in the description that follows and/or learned by practice of the presented exemplary embodiments.

BRIEF DESCRIPTION OF THE DRAWINGS

These and/or other aspects will become apparent and more readily appreciated from the following description of the exemplary embodiments, taken in conjunction with the accompanying drawings.

DETAILED DESCRIPTION

Figure 1:
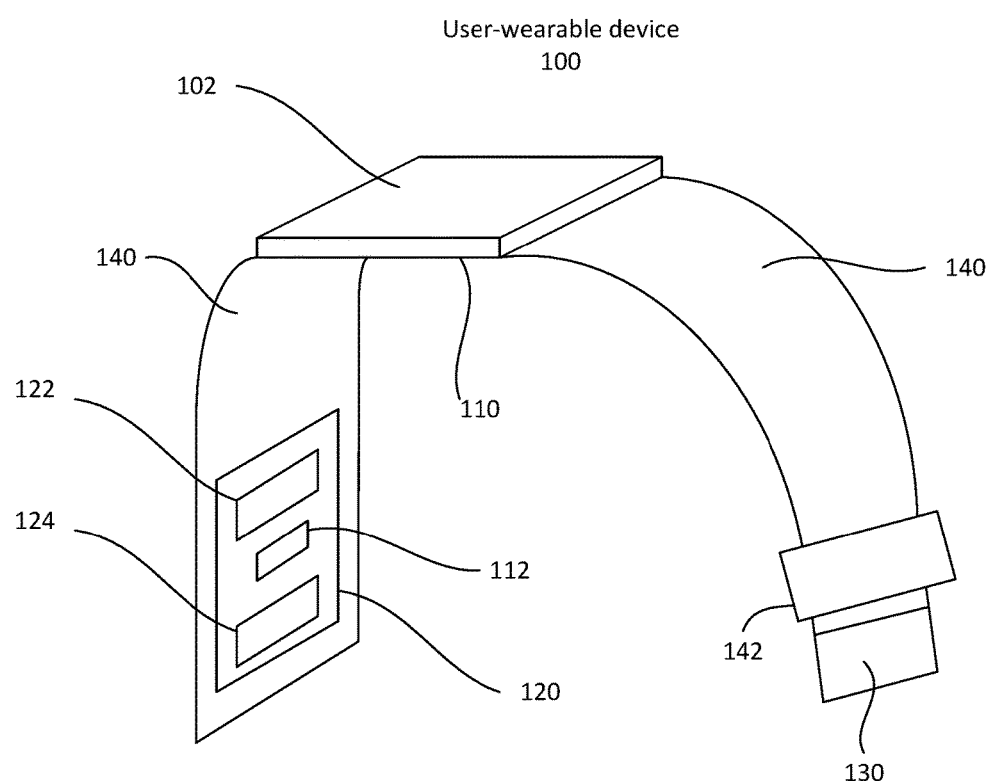
FIG. 1 is a diagram illustrating an electronic device in accordance with an embodiment of the present disclosure.

Advantages and features of one or more embodiments of the present disclosure may be understood more readily by reference to the following detailed description of the embodiments and the accompanying drawings.

In this regard, the present embodiments should not be construed as being limited to the descriptions set forth herein. Rather, these embodiments are provided as examples so that this disclosure will be thorough and complete and will fully convey the concept of the present embodiments to one of ordinary skill in the art. The appended claims illustrate some of the embodiments of the present disclosure.

Like reference numerals refer to like elements throughout the specification. All terms including descriptive or technical terms used herein should be construed as having meanings that are obvious to one of ordinary skill in the art. When a term has an ambiguous meaning due to evolving of language, precedent cases, or the appearance of new technologies, the meaning of a term used in this disclosure should first be clarified by its usage and/or definition in this disclosure. If further clarification is needed, the term should then be clarified as one of ordinary skill in the art would have understood the term in context of the disclosure at the time of the disclosure.

When a part "includes" or "comprises" an element, unless there is a particular description contrary thereto, the part can further include other elements. The term "unit" in the embodiments of the present disclosure means a software component or a hardware component that performs a specific function. The hardware component may include, for example, a field-programmable gate array (FPGA) or an application-specific integrated circuit (ASIC).

Software component may refer to executable code and/or data used by the executable code in an addressable storage medium. Thus, software components may be, for example, object-oriented software components, class components, and task components, and may include processes, functions, attributes, procedures, subroutines, segments of program code, drivers, firmware, micro codes, circuits, data, a database, data structures, tables, arrays, or variables.

A function provided by a "unit" may be divided into additional components and "units."

Reference will now be made in detail to embodiments, examples of which are illustrated in the accompanying drawings. In this regard, the present embodiments may have different forms and should not be construed as being limited to the descriptions set forth herein.

In the following description, well-known functions or constructions are not described in detail so as not to obscure the embodiments with unnecessary detail.

FIG. 1 is a diagram illustrating an electronic device in accordance with an embodiment of the present disclosure. Referring to FIG. 1, an electronic device, which includes a user-wearable device 100, has a display 102, processors 110 and 112, a sensor module 120, a battery 130, a band 140, and a clasp 142. The sensor module 120 may include sensors 122 and 124.

Although the user-wearable device 100 may be worn on a wrist, various embodiments of the disclosure need not be so limited. The user-wearable device 100 may also be designed to be worn on other parts of the body, such as, for example, on an arm (around the forearm, the elbow, or the upper arm), on a leg, around the chest, around the head like a headband, around the throat like a "choker," and on an ear. The user-wearable device 100 may be able to communicate with other electronic devices such as, for example, a smart phone or a laptop. This will be described in more detail with respect to FIG. 3.

The display 102 may output monitored physiological signals from the user's body for viewing by the user and/or others. The signals being monitored may be referred to as biosignals or biometric data. The monitored signals may be, for example, pulse rate, pulse morphology (shape), and/or pulse spacing (inter-beat intervals). The display 102 may also output instructions to the user or others in the use of the user-wearable device 100 or use of other measurement devices, as well as status and diagnostic results.

The processor 110 may process the monitored signals to determine whether a more detailed monitoring and/or a different type of monitoring may be needed. The sensor module 120 may include, for example, the sensors 122 and 124 that touch the user's wrist when the user-wearable device 100 is worn by a user. The processor 112 may control the sensors 122 and 124, and may also process the signals monitored by the sensors 122 and 124. For example, the processor 112 may filter noise from the signals monitored by the sensors 122 and 124. Various embodiments of the disclosure may have the processor 110 also perform the functions of the processor 112. Various embodiments of the disclosure may also have different number of sensors.

The sensor 122 may be, for example, a PPG sensor that is used to continuously or near continuously monitor pulse related information. The sensor 124 may be a more sensitive type of a PPG sensor that is used when the processor 110 determines that further signal monitoring is needed using a more sensitive sensor, a sensor that is more relevant to the specific signals being monitored, or a sensor that may have greater use acceptance by, for example, medical professionals for monitoring certain biosignals or biometric data. That is, a sensor with greater sensitivity, specificity, and/or acceptability may be used. The sensor 124 may be, for example, an ECG sensor.

The battery 130 may be configured to provide power for the user-wearable device 100. The battery 130 may be charged using a wired charging system or a wireless charging system. The band 140 may be wrapped around a wrist and the user-wearable device 100 may be held on the wrist by using the clasp 142.

The user-wearable device 100 may provide continuous monitoring, or periodic monitoring. The specific type of monitoring may be design and/or implementation dependent, and may also include an option that allows the user to select the type of monitoring. Periodic monitoring may alternate monitoring period and a non-monitoring period. Periodic monitoring may be to allow for longer battery life.

Figure 2:
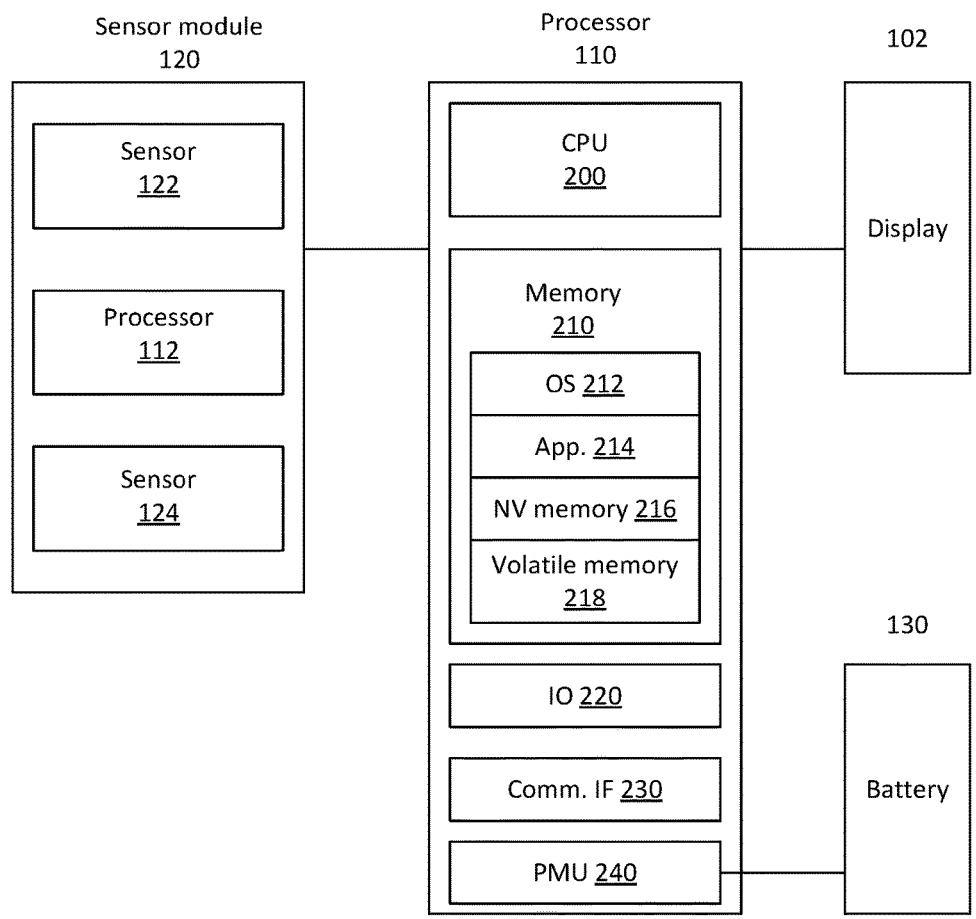
FIG. 2 is a high-level block diagram of an electronic device in accordance with an embodiment of the present disclosure.

FIG. 2 is a high-level block diagram of an electronic device in accordance with an embodiment of the present disclosure. Referring to FIG. 2, there is shown the display 102, the processor 110, the sensor module 120, and the battery 130. Output to the display 102 may be controlled by the processor 110. The display 102 may also include input devices (not shown) such as, for example, buttons, dials, touch sensitive screen, and microphone.

The processor 110 may include a CPU 200, memory 210, an input/output (IO) interface 220, a communication interface 230, and a power management unit (PMU) 240. While the processor 110 is described as comprising these various devices, other embodiments may use other architectures where the different functionalities are grouped differently. For example, the grouping may be in different integrated circuit chips. Or the grouping may be combining different devices such as the IO interface 220 and the communication interface 230 together.

The CPU 200 may control operation of the sensor module 120 as well as receive monitored signals from the sensor module 120. The CPU 200 may control the user-wearable device 100, including processing the monitored signals from the sensor module 120, displaying the processed signals on the display 102, receiving input from the display 102, interfacing with various devices via the IO interface 220 or the communication interface 230 by executing instructions in the memory 210. The IO interface 220 may be used by the CPU 200 to interface with the display 102.

The processor 112 may operate using different architectures in different embodiments. For example, the processor 112 may use the memory 210 to store instructions to execute, or the processor 112 may have its own memory (not shown) for its instructions. Although some embodiments have separate processors 110 and 112, the various embodiments need not be limited so. There may be one processor 110 that controls the functionality of the user-wearable device 100, or there may be multiple processors for the user-wearable device 100.

The memory 210 may include non-volatile memory 216 and volatile memory 218. The operating system and applications may be stored in the non-volatile memory 216. Various embodiments of the disclosure may use different memory architectures that are design and or implementation dependent.

The communication interface 230 may allow the user-wearable device 100 to communicate with other devices via, for example, a wired protocol such as USB or a wireless protocol such as Bluetooth, Near Field Communication (NFC), and WiFi. The PMU 240 may control receiving power from an outside source, charging the battery 130, as well as allocation of power to the different parts of the user-wearable device 100.

Figure 3:
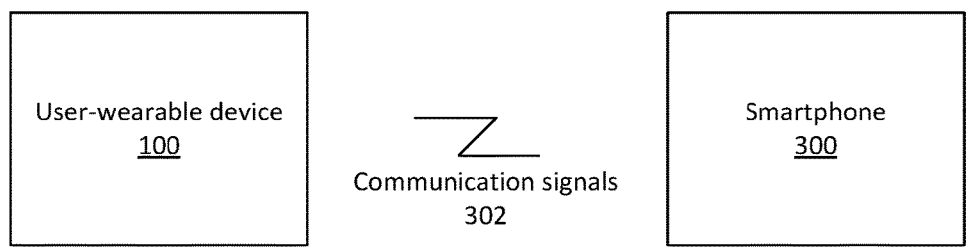
FIG. 3 is an illustration of an electronic device in a communication network in accordance with an embodiment of the present disclosure.

FIG. 3 is an illustration of an electronic device in a communication network in accordance with an embodiment of the present disclosure. Referring to FIG. 3, there is shown the user-wearable device 100 and a smartphone 300. The user-wearable device 100 may communicate with the smartphone 300 using the communication interface 230. The communication may be via communication signals 302 between the user-wearable device 100 and the smartphone 300. The communication signals 302 may be via a wired communication protocol or a wireless communication protocol. Although not shown, the communication signals 302 may be sent via one or more communication units between the user-wearable device 100 and the smartphone 300. For example, the user-wearable device 100 and the smartphone 300 may belong to the same network or different networks.

One of the applications 214 of the user-wearable device 100 may allow the smartphone 300 to control at least some operation of the user-wearable device 100 via the communication signals 302. For example, user-wearable device 100 may output to the display 102 a result of the processing by the processor 110, and/or the same result may be transmitted to the smartphone 300. The user may then select an option either on the user-wearable device 100 or on the smartphone 300.

The options may be, for example, to use the sensor 124 on the user-wearable device 100 that is more sensitive than the sensor 122 that was used up to now, to use another monitoring device that may need to be put on by the user, or to repeat monitoring with the sensor 122.

Since the smartphone 300 has a larger display, it may be easier for the user to select an option on the smartphone 300 rather than on the user-wearable device 100. However, it should be noted that the smartphone 300 may not generally be necessary for operation of the user-wearable device 100.

Figure 4:
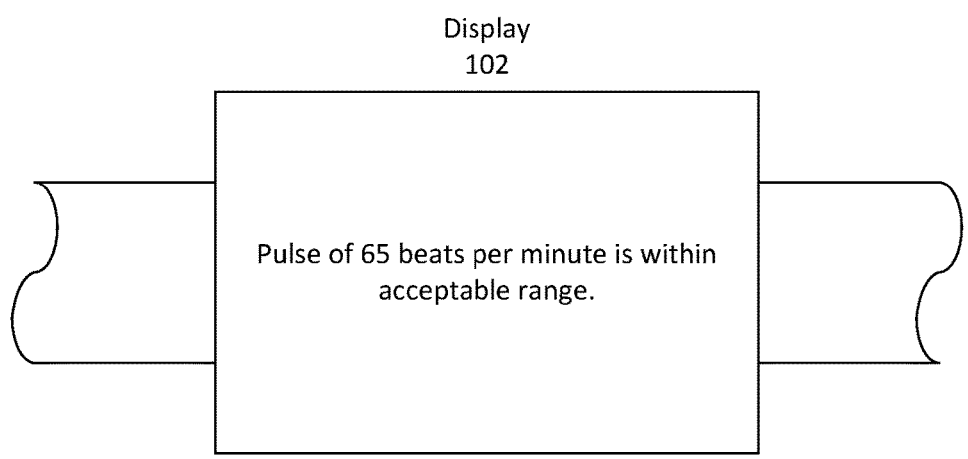
FIG. 4 is an exemplary notification by the electronic device to the user for acquiring signals in a second mode.

FIG. 4 is an exemplary notification by the electronic device to the user for acquiring signals in the second mode of monitoring. Referring to FIG. 4, status may be shown on the display 102 when no user intervention is required. The status may indicate, for example, that no anomalies have been detected in the first mode of monitoring where the user-wearable device 100 monitors the user continuously or near continuously with no need for intervening action by the user. The status may be, for example, that the sensor 122, which may measure the pulse of the user in some embodiments, does not detect the pulse to be out of a normal range for a typical person having the user's characteristics. The characteristics may include, for example, sex, height, and weight. These characteristics may be entered directly into the user-wearable device 100 or via, for example, the smartphone 300.

When the processor 110, which may be referred to as a diagnostic processor, determines that the monitored signals from the sensor 122 indicates that further measurements need to be taken, instructions to the user may be displayed on the display 102. The instructions may indicate, for example, that the user needs to adjust the user-wearable device 100 to be tighter on the wrist so that the sensor 124, which may be a more sensitive sensor than the sensor 122, may acquire more accurate reading. Or, the instructions may indicate that the user should rest for a period of time before continuing with further monitoring in the second mode. Or, the instructions may indicate that the user needs to put on another more specialized monitoring device.

Various embodiments of the disclosure may include different instructions for different types of monitoring, including instructing the user to consult a medical professional. Accordingly, the user-wearable device 100 may have different levels of instructions and monitoring depending on the needs of the user and/or the medical professional.

According to some embodiments, the sensor 122 may monitor background-acquired signal data in the first mode to determine whether to enter triage states in the second mode. Entering the triage states may require user involvement (e.g., a change in fit or behavior), to trigger the use of a second sensor device such as the sensor 124 that may have higher power consumption than the first sensor device such as the sensor 122. The higher power may be needed for improved signal quality, to change a type of signal acquisition and/or processing the acquired signals, and/or to perform an advanced method of physiological monitoring of the user.

Figure 5:
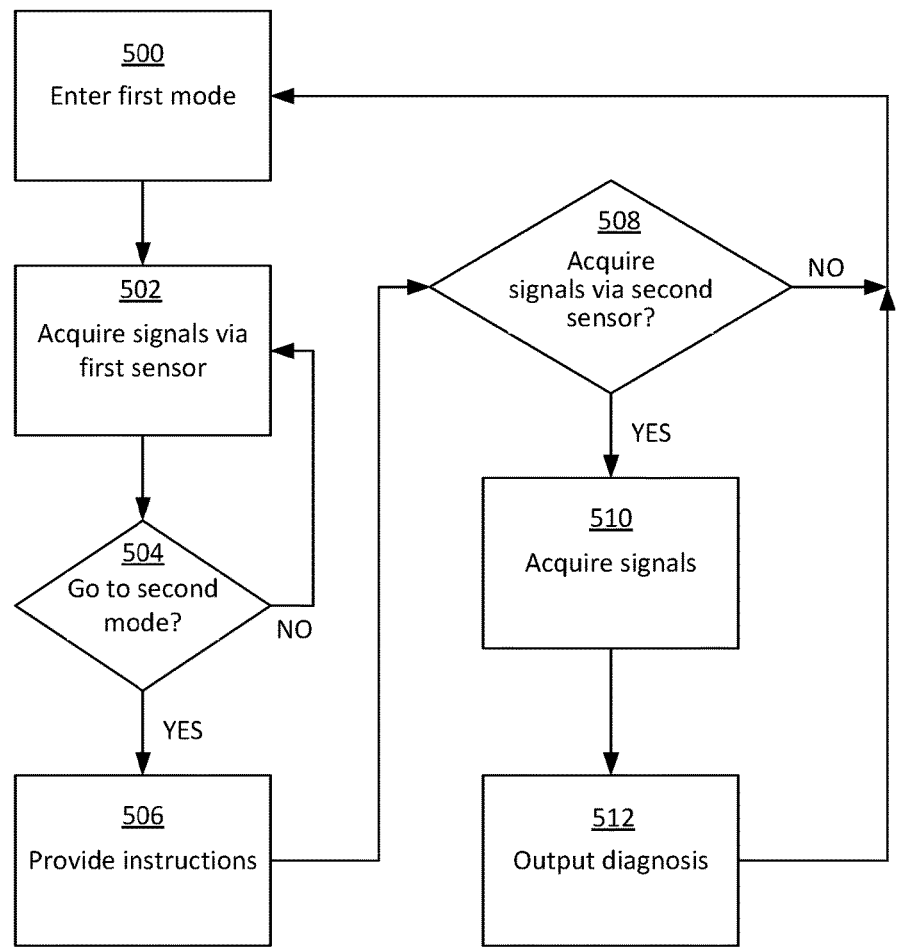
FIG. 5 is an exemplary flowchart for determining whether to enter a second mode.

FIG. 5 is an exemplary flowchart for determining whether to enter a second mode. Referring to FIG. 5, there is shown operations 500 to 512. At 500, the user-wearable device 100 enters the first mode to monitor some of the user's biosignals or biometric data via the sensor 122. The sensor 122 may acquire sensor signals that may be of low quality due to non-ideal contact between the sensor 122 and the user, and due to the sensor 122 being less sensitive than, for example, the sensor 124 or an external sensor (not shown).

If the sensor 122 is a PPG sensor, the acquired biosignals will be related to the user's pulse. The user-wearable device 100 may start the acquisition upon being turned on by operating in the background without user input during the acquisition. For some types of biosignal acquisition, the user may need to enter some information prior to the acquisition. The information may be, for example, sex, height, and weight that may be relevant to processing the biosignals.

At 502, the sensor 122 acquires biosignals. At 504, the processors 110 and/or 112 determine whether to proceed to a second mode based on the acquired biosignals. The processors 110 and/or 112 may determine that the acquired biosignals from the sensor 122 may not be normal, for example, based on a predetermined threshold, or because the acquired biosignals are different from prior biosignals from the user. The prior biosignals may have been acquired in previous sessions or may have been downloaded to the user-wearable device 100 and stored in the memory 210.

If the processors 110 and/or 112 determine not to proceed to the second mode, the sensor 122 continues to acquire biosignals from the user at 502. If the processors 110 and/or 112 determine to enter the second mode, the user-wearable device 100 displays instructions on the display 102 at 506. The instructions may be, for example, to further acquire biosignals using the more sensitive sensor 124 or an external sensor (not shown). Or, the instructions may be for some processes that do not require additional sensor measurements. For example, the instruction may be to visit a doctor for more detailed tests.

The sensor 124 may be a traditional sensor and/or provide more relevant and/or sensitive sensor signals than the sensor 122. Usage of the sensor 124 may require the user to perform a specific procedure that provides greater diagnostic and/or sensing capabilities. For example, the user may be instructed to tighten the band 140 to allow better contact between the sensor 124 and the user's skin. Or the user may be told to pose or hold still for a period of time, or to hold the sensor module 120 or an external sensor on the user's body in one or more specific positions/orientations to maximize signal quality from a body part.

Having the user pose in a specific position may allow observation of specific measurable quantities that are not otherwise observable. For example, the user might be asked to raise their arm to see how the hydrostatic pressure changes impact the blood flow in their arm. Without having the user move their arm, this information may not be able to be acquired.

In another embodiment, the sensor 122 may acquire skin temperature, and the user-wearable device 100 may determine that the temperature is higher than a predetermined threshold temperature for the user. The display 102 may output an instruction for the user to perform temperature measurement using an oral or temporal thermometer.

In another embodiment, the biosignals acquired by the sensor 122 may indicate spectral characteristics of significantly increased blood alcohol levels. Accordingly, the user-wearable device 100 may provide instructions to the user on the display 102 to perform a horizontal gaze nystagmus test to determine a sobriety state of the user and his/her capability to operate a vehicle.

In another embodiment, the sensor 122 may acquire GSR signals from a wrist-worn device, and the user-wearable device 100 may determine that the GSR signals indicates a level of sympathetic nervous system activation that does not satisfy a predetermined threshold for the user. This may trigger the user-wearable device 100 to provide one or more questions to the user to determine his/her cognitive state in an attempt to recognize an altered mental state.

At 508, if biosignals are to be acquired using a more sensitive sensor, the user-wearable device 100 may acquire biosignals at 510 with the sensor 124 that may be more sensitive than the sensor 122. The biosignals may be processed to determine a diagnosis or next step of action. If biosignals are not to be acquired by the second sensor of the user-wearable device 100, then, in an embodiment of the disclosure, the user-wearable device 100 may enter the first mode at 500. This may occur, for example, if instructions were given at 506 to visit a doctor or if an external sensor is to be used for further monitoring of biosignals. Additionally, while an embodiment may enter the first mode at 500 if further monitoring is not needed using the second sensor, various embodiments of the disclosure need not be so limited. For example, the user-wearable device 100 may enter a stand-by state until the user enters an input to start the biosignal acquisition at 500. The specific action to be taken will depend on design and/or implementation decisions.

At 512, after processing signals acquired by the sensor 124 the user may be given a result of the biosignal monitoring. The user may be told to perform, for example, an electro-cardiogram (ECG) recording to diagnose for heart rhythm anomalies/abnormalities. Even if the sensor 124 is an ECG sensor, in some instances there may be instructions to have another ECG recording performed by an external device. The monitoring by an external device may need to be done at a doctor's office, or possibly by the user if the user has an external device able to make ECG recordings.

Various embodiments have described the user-wearable device 100 to be directed to monitoring some of a user's biosignals or biometric data; however other embodiments may monitor different biosignals than those mentioned in this disclosure.

Additionally, while some actions may have been taken due to instructions at 506 (e.g., skin temperature, blood alcohol level, GSR, and signals), various embodiments may continue on to take more accurate measurements at 508 and 510.

Various embodiments of the disclosure may be written as computer programs and may be implemented in general-use digital computers that execute the programs using a non-transitory computer-readable recording medium.

Non-transitory computer-readable recording medium may include, for example, magnetic storage media (e.g., ROM, floppy disks, and hard disks), and optical recording media (e.g., CD-ROMs, or DVDs).

While various embodiments of the disclosure have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What is claimed is:

1. A non-transitory machine-readable medium storing machine executable instructions that when executed causes a computing system to control operations comprising:
   acquiring first signals in a first mode from a user via a first sensor of a user-wearable device;
   processing the first signals to determine whether to enter a second mode to provide further information to the user; and
   upon determining to enter the second mode:
      providing, on a display, at least one instruction to the user appropriate for the second mode;
      determining whether to acquire second signals with a second sensor based on determining that the user has complied with the at least one instruction; and
      upon determining to acquire the second signals:
         acquiring the second signals; and
         providing, on the display, at least one follow-up instruction to the user based on processing the acquired second signals.

2. The non-transitory machine-readable medium of claim 1, further comprising machine executable instructions for acquiring the first signals periodically in the first mode.

3. The non-transitory machine-readable medium of claim 1, further comprising machine executable instructions for acquiring the first signals continuously in the first mode.

4. The non-transitory machine-readable medium of claim 1, further comprising machine executable instructions for instructing the user to perform at least one of: have the user-wearable device in a specific position and/or orientation, and pose in a specific position.

5. The non-transitory machine-readable medium of claim 1, further comprising machine executable instructions for using a second sensor in the user-wearable device to acquire second signals in the second mode.

6. The non-transitory machine-readable medium of claim 5, wherein the second sensor compared to the first sensor has at least one of: greater sensitivity, greater specificity, and greater use acceptance for acquiring the second signals.

7. The non-transitory machine-readable medium of claim 1, further comprising machine executable instructions for, upon determining to enter the second mode, providing at least one question to the user to appraise a cognitive state of the user based on the user answering the at least one question.

8. The non-transitory machine-readable medium of claim 1, wherein determining whether to acquire the second signals does not depend on an input from the user.

9. The non-transitory machine-readable medium of claim 1, wherein the first mode comprises monitoring the first signals to determine whether to enter a triage state in the second mode.

10. The non-transitory machine-readable medium of claim 1, wherein the second mode comprises one or more of: acquiring the second signals with improved signal quality compared to a signal quality of the first signals, changing a type of signal acquisition for acquiring the second signals, changing processing of the acquired first signals and/or the second signals, and performing an advanced method of physiological monitoring of the user.

11. A system comprising:
a first sensor of a user-wearable device configured to acquire first signals in a first mode from a user;
a display configured to output visual information to the user; and
a diagnostic processor configured to:
process the first signals to determine whether to enter a second mode to provide further information to the user; and
upon determining to enter the second mode:
provide, on the display, at least one instruction to the user appropriate for the second mode;
determine whether to acquire second signals with a second sensor based on determining that the user has complied with the at least one instruction; and
upon determining to acquire the second signals:
acquire the second signals; and
provide, on the display, at least one follow-up instruction to the user based on processing the acquired second signals.

12. The system of claim 11, wherein the first signals are acquired periodically in the first mode.

13. The system of claim 11, wherein the first signals are acquired continuously in the first mode.

14. The system of claim 11, wherein the diagnostic processor is configured to instruct the user to perform at least one of: have the user-wearable device in a specific position and/or orientation, and pose in a specific position.

15. The system of claim 11, wherein the user-wearable device consumes more power in the second mode than in the first mode.

16. The system of claim 11, further comprising a second sensor in the user-wearable device configured to acquire second signals in the second mode.

17. The system of claim 16, wherein the second sensor compared to the first sensor has at least one of: greater sensitivity, greater specificity, and greater use acceptance for acquiring the second signals.

18. The system of claim 11, wherein the diagnostic processor is configured to, upon determining to enter the second mode, provide at least one question to the user to appraise a cognitive state of the user based on the user answering the at least one question.

19. The system of claim 11, wherein the diagnostic processor is further configured to, upon determining to not acquire the second signals, enter a standby mode until the user indicates via an input to enter the first mode to continue to acquire a new set of the first signals.

20. The system of claim 11, wherein the first sensor is further configured to, upon the diagnostic processor determining to not enter the second mode, continue to acquire the first signals.

21. A method comprising:
acquiring first signals in a first mode from a user by a first sensor of a user-wearable device;
processing the first signals by a diagnostic processor to determine whether to enter a second mode to provide further information to the user; and
upon determining to enter the second mode:
providing, on a display, at least one instruction to the user appropriate for the second mode;
determining whether to acquire second signals with a second sensor based on determining that the user has complied with the at least one instruction; and
upon determining to acquire the second signals:
acquiring the second signals; and
providing, on the display, at least one follow-up instruction to the user based on processing the acquired second signals.

* * * * *